United States Patent
Goodnow et al.

(10) Patent No.: US 8,047,996 B2
(45) Date of Patent: Nov. 1, 2011

(54) SYSTEM AND METHOD FOR REDUCING ANGULAR GEOMETRIC DISTORTION IN AN IMAGING DEVICE

(75) Inventors: John W. Goodnow, Arlington, MA (US); Paul A. Magnin, Andover, MA (US)

(73) Assignee: Volcano Corporation, San Diego, CA (US)

( * ) Notice: Subject to any disclaimer, the term of this patent is extended or adjusted under 35 U.S.C. 154(b) by 1675 days.

(21) Appl. No.: 11/261,635

(22) Filed: Oct. 31, 2005

(65) Prior Publication Data
US 2007/0106155 A1 May 10, 2007

(51) Int. Cl.
*A61B 8/00* (2006.01)
(52) U.S. Cl. ........ 600/463; 600/437; 600/462; 600/466; 600/467
(58) Field of Classification Search .................. 600/407, 600/437, 462–463, 466–467, 473, 476; 382/128; 73/570, 584, 596, 618, 622–623
See application file for complete search history.

(56) References Cited

U.S. PATENT DOCUMENTS

| | | |
|---|---|---|
| 3,542,014 A | 11/1970 | Peronneau |
| 3,779,234 A | 12/1973 | Eggleton et al. |
| 3,817,089 A | 6/1974 | Eggleton et al. |
| 3,827,115 A | 8/1974 | Bom |
| 3,938,502 A | 2/1976 | Bom |
| 4,316,390 A | 2/1982 | Kretz |
| 4,391,282 A | 7/1983 | Ando et al. |
| 4,408,612 A | 10/1983 | Utsugi |
| 4,489,728 A | 12/1984 | Matsuo et al. |
| 4,587,972 A | 5/1986 | Morantte, Jr. |
| 4,794,931 A | 1/1989 | Yock |
| 4,805,155 A | 2/1989 | Shiraishi et al. |
| 4,841,977 A | 6/1989 | Griffith et al. |
| 4,899,757 A | 2/1990 | Pope, Jr. et al. |
| 4,911,170 A | 3/1990 | Thomas, III et al. |

(Continued)

FOREIGN PATENT DOCUMENTS

NL 87-00632 10/1988

OTHER PUBLICATIONS

Evans et al., "Arterial Imaging with a New Forward-Viewing Intravascular Ultrasound Catheter, I, Initial Studies," Circulation, vol. 89, No. 2, pp. 712-717, Feb. 1994.

(Continued)

*Primary Examiner* — Tse Chen
*Assistant Examiner* — Peter Luong
(74) *Attorney, Agent, or Firm* — Haynes and Boone, LLP

(57) ABSTRACT

A system and method are provided for significantly reducing or substantially eliminating angular geometric distortions in devices designed for imaging and/or inspection of an interior portion or surface of a cavity. A series of processing steps or methods may be employed to eliminate Non-Uniform Rotational Distortion (NURD) in such devices, for example, unidirectional and bi-directional intravascular ultrasonic (IVUS) imaging systems. The system may include a processor and an electronic module which control operation of a transducer assembly provided at a distal end of a catheter assembly. The system invokes a first processing step or method to collect and store raw angle and line data, as well as one or more of second and third processing steps or methods which adjust for NURD experienced during backlash of a bi-directional imaging system and a fourth processing step or method which performs a line-to-line correlation function.

61 Claims, 16 Drawing Sheets

U.S. PATENT DOCUMENTS

| | | | |
|---|---|---|---|
| 4,917,097 A | 4/1990 | Proudian et al. | |
| 4,951,677 A | 8/1990 | Crowley et al. | |
| 5,000,185 A | 3/1991 | Yock | |
| 5,054,492 A | 10/1991 | Scribner et al. | |
| 5,115,814 A | 5/1992 | Griffith et al. | |
| 5,127,409 A | 7/1992 | Daigle | |
| 5,131,397 A | 7/1992 | Crowley | |
| 5,176,141 A | 1/1993 | Bom et al. | |
| 5,186,177 A | 2/1993 | O'Donnell et al. | |
| 5,203,338 A | 4/1993 | Jang | |
| 5,240,003 A | 8/1993 | Lancee et al. | |
| 5,243,988 A | 9/1993 | Sieben et al. | |
| 5,271,400 A | 12/1993 | Dumoulin et al. | |
| 5,271,402 A | 12/1993 | Yeung et al. | |
| 5,284,148 A | 2/1994 | Dias et al. | |
| 5,313,949 A | 5/1994 | Yock | |
| 5,321,501 A | 6/1994 | Swanson et al. | |
| 5,345,940 A | 9/1994 | Seward et al. | |
| 5,353,798 A | 10/1994 | Sieben | |
| 5,361,768 A | 11/1994 | Webler et al. | |
| 5,368,035 A | 11/1994 | Hamm et al. | |
| 5,373,845 A | 12/1994 | Gardineer et al. | |
| 5,373,849 A | 12/1994 | Maroney et al. | |
| 5,375,602 A | 12/1994 | Lancee et al. | |
| 5,377,685 A | 1/1995 | Kazi et al. | |
| 5,379,772 A | 1/1995 | Imran | |
| 5,439,000 A | 8/1995 | Gunderson et al. | |
| 5,469,853 A | 11/1995 | Law et al. | |
| 5,485,845 A | 1/1996 | Verdonk et al. | |
| 5,588,432 A | 12/1996 | Crowley | |
| 5,594,842 A | 1/1997 | Kaufman et al. | |
| 5,606,454 A | 2/1997 | Williams et al. | |
| 5,651,366 A | 7/1997 | Liang et al. | |
| 5,699,806 A | 12/1997 | Webb et al. | |
| 5,921,934 A | 7/1999 | Teo | |
| 6,066,096 A | 5/2000 | Smith et al. | |
| 6,095,981 A | 8/2000 | McGahan | |
| 6,120,455 A | 9/2000 | Teo | |
| 6,221,020 B1 * | 4/2001 | Lysyansky et al. | 600/453 |
| 6,267,727 B1 | 7/2001 | Teo | |
| 6,423,002 B1 * | 7/2002 | Hossack | 600/439 |
| 6,445,939 B1 | 9/2002 | Swanson et al. | |
| 6,450,964 B1 | 9/2002 | Webler | |
| 6,457,365 B1 | 10/2002 | Stephens et al. | |
| 6,780,157 B2 | 8/2004 | Stephens et al. | |
| 6,860,855 B2 | 3/2005 | Shelby et al. | |
| 6,863,676 B2 | 3/2005 | Lee et al. | |
| 6,960,172 B2 | 11/2005 | McGuckin et al. | |
| 7,022,082 B2 | 4/2006 | Sonek et al. | |
| 7,024,025 B2 * | 4/2006 | Sathyanarayana | 600/467 |
| 7,025,765 B2 | 4/2006 | Balbierz et al. | |
| 2002/0032437 A1 | 3/2002 | Andrews et al. | |
| 2002/0183826 A1 | 12/2002 | Dorn et al. | |
| 2003/0125757 A1 | 7/2003 | Patel et al. | |
| 2004/0113909 A1 | 6/2004 | Fenney et al. | |
| 2005/0107688 A1 | 5/2005 | Strommer | |
| 2005/0128730 A1 | 6/2005 | Shindoh | |

OTHER PUBLICATIONS

Ng et al., "Arterial Imaging with a New Forward-Viewing Intravascular Ultrasound Catheter, II, Three-Dimensional Reconstruction and Display of Data," Circulation, vol. 89, No. 2, pp. 718-723, Feb. 1994.

Liang, D.H., "A Forward-Viewing Intravascular Ultrasound Catheter Suitable for Intracoronary Use," Biomedical Instrumentation & Technology, Jan./Feb. 1997. pp. 45-53.

Von Birgelen C., et al., "Preintervention Lesion Remodeling affects Operative Mechanisms of Balloon Optimized Directional Coronary Atherectany Procedures: a volumetric study with three dimensional intravascular ultrasound," Heart 2000, vol. 83, pp. 192-197.

Catmull, E., "A Subdivision Algorithm for Computer Display of Curved Surfaces," Ph.D. Thesis, Report UTEC-CSc-74-133, Computer Science Department, University of Utah, Salt Lake City, UT, Dec. 1974. Also in "Computer Display of Curved Surfaces," Proc. IEEE Conf. on Computer Graphics, Pattern Recognition and Data Structures, May 1975.

Blinn, J.F., and M.E. Newell, Texture and Reflection in Computer Generated Images, Communications of the ACM, 19(10), Oct. 1976, pp. 542-547.

Heckbert, P.S., "Survey of Texture Mapping," IEEE Computer Graphics and Applications, 6(11), Nov. 1986, pp. 56-67.

Kimura et al., "Can Intravascular Ultrasound Yield Accurate Measuremetns of Vascular Anatomy? Documentation of the Critical Improtance of Uniform Rotational Velocity" 1994, vo. 1A(484) p. 173A, JACC.

Bom et al., "Early and Recent Interluminal Ultrasound Devices" International Journal of Cardiac Imaging 4:79-88, 1989, 1989 Kluwer Academic Publishers, Printed in the Netheralnds.

Bom et al., "Intra-Arterial Ultrasonic Imaging for Recanalization by Spark Erosion," Ultrasound in Med. & Biol., vol. 14, No. 4, pp. 257-261, 1988.

Harm ten Hoff et al., "Imaging artifacts in mechanically driven ultrasound catheters" 1989, vol. 4, pp. 195-199, International Journal of Cardiac Imaging.

Slager et al., "Removal of Cardiovascular Obstructions by Spark Erosion," public presentation of dissertation Dec. 17, 1997 at 3:45 PM, later printed in "Spark Erosion Under Ultrasound Guidance," Ch. 8, pp. 81-90, ICG Printing Dordrecht.

Slager et al., "Vaporization of Atherosclerotic Plaque by Spark Erosion", JACC, Jun. 1985, 5:00. 1382-1386-6.

Slager, et al., "Spark Erosion and Its Combination with Sensing Devices for Ablation of Vascular Lesions", Chapter 13, in John H.K. Vogel and Spencer B. Kin, III, Interventional Cardiology: Future Directions, The C.V. Mosby Company, St. Louis, 1989, pp. 157-169. Presented Sep. 26, 1987 Santa Barbara.

* cited by examiner

Figure 2

Data Table

| n | Angle(n) | EchoData(n,t) |
|---|----------|---------------|
| 1 | Angle(1) | EchoData(1,t) |
| 2 | Angle(2) | EchoData(2,t) |
| 3 | Angle(3) | EchoData(3,t) |
| 4 | Angle(4) | EchoData(4,t) |
| 5 | Angle(5) | EchoData(5,t) |
| 6 | Angle(6) | EchoData(6,t) |
| ... | ... | ... |
| N | Angle(N) | EchoData(N,t) |

50

SYSTEM AND METHOD FOR REDUCING ANGULAR GEOMETRIC DISTORTION IN AN IMAGING DEVICE

BACKGROUND OF THE INVENTION

1. Field of the Invention

This invention relates to a system and method for reducing angular geometric distortion in an imaging device.

2. Background of the Related Art

A number of diagnostic tools are used in the field of Interventional Cardiology to diagnose and treat heart disease. Among other things, Intravascular Ultrasonic (IVUS) imaging systems are used to estimate an extent of coronary artery plaque, allowing an interventionalist to detect heart disease, estimate the severity of the disease and its effect on blood flow, and choose appropriate therapies. One such system is a fluoroscopy system, which injects a radio-opaque contrast dye into the bloodstream, and then uses a real time x-ray imaging technique to watch as the contrast dye passes through the vascular tree. However, fluoroscopy systems do not image the vessel tissue, but rather the blood pool inside the vessel lumen.

In an attempt to obtain an image of the vessel wall, and not just the blood pool, ultrasonic imaging transducers are mounted at the distal end of catheters and positioned in the coronary arteries. This approach allows the visualization of the tissues of the artery walls, and more particularly, visualization of the atherosclerotic plaque that forms in these vessels. However, these images are compromised in that the assumed angular orientation of the ultrasonic transducer at the distal tip of the catheter is not, in fact, the actual orientation of the transducer.

More particularly, in many IVUS imaging systems, the proximal end of a torque cable is spun at a uniform velocity by an electric motor. For example, a motor rotated at approximately 1800 RPM generates a complete circular cross section at a rate of approximately 30 frames, or images, each second. However, a catheter has a number of bends and twists in its length necessary to get from the entry point into the human body to a point at which an image is acquired. One of the most common distortions generated by these types of IVUS systems is Non-Uniform Rotational Distortion (NURD).

NURD can be caused by a number of different sources, including, for example, friction between the spinning torque cable and the stationary sheath that encloses the cable, or the torque cable and transducer assembly being not perfectly cylindrically symmetrical, causing the cable to resist bending more at some angles than at other angles. When rotated, these asymmetries will cause the cable to store more energy in some angular orientations and then to release that energy as the cable is rotated past that angle. In either case, the angular velocity of the transducer varies with each cycle even if the motor maintains a constant speed at the proximal end of the catheter. In many situations, an absolute angular orientation of a particular lesion or section of a lesion may be critical in performing an accurate, timely diagnosis and prescribing appropriate treatment. Thus, it is important to substantially eliminate, or at least significantly reduce, NURD so that these measures of angular extent are accurate and reliable.

To this end, new IVUS systems have been proposed in which the catheter is manually rotated in either direction so as to produce an image of a sector of an artery, rather than spinning the catheter in a single direction. However, this change in rotational direction leads to another form of NURD caused by the "windup" and resulting "backlash" of the transducer when the rotational direction is changed. Electronically steered imaging systems produce images without rotating the transducers on the distal end of the catheter, and thus do not produce any rotational distortion. However, this comes at the expense of increased transducer, catheter, and imaging system complexity and cost.

SUMMARY OF THE INVENTION

An object of the invention is to solve at least the above problems and/or disadvantages and to provide at least the advantages described hereinafter.

Embodiments of the invention are directed to a system and method for reducing angular geometric distortion in an imaging device. The system and method according to the invention may be utilized with any type of device used to image and/or inspect an interior portion of a cavity, such as a substantially tubular cavity, in which it is advantageous to significantly reduce or substantially eliminate angular geometric distortion.

Further, embodiments of the invention are directed to a system and method capable of significantly reducing or substantially eliminating NURD in both continuously rotated IVUS systems, in which the direction of rotation remains substantially constant, and in manually rotated IVUS systems, in which the direction of rotation is changed and windup and backlash NURD are also present.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein:

FIG. 2 is an exemplary data table generated and stored by the processor shown in FIG. 1B;

DETAILED DESCRIPTION OF PREFERRED EMBODIMENTS

The following detailed description of embodiments of the invention is discussed in the context of NURD reduction for an IVUS system. However, the invention may be utilized with any type of device used to image and/or inspect an interior portion of a cavity, such as a substantially tubular cavity, in which it is advantageous to significantly reduce or substantially eliminate angular geometric distortion.

NURD reduction for an IVUS system can be viewed as a process that more accurately assigns angles that are associated with each acoustic line in an IVUS frame compared to angles that are assumed to be present at a proximal end of a catheter as imaging data is collected. The systems and methods according to certain embodiments of the invention apply algorithms which may be implemented in either hardware or software, and may operate in real time on data as it is collected from a transducer to produce images without any objectionable distortions caused by NURD.

It should be noted that, as discussed above, medical devices, and more particularly, IVUS devices, are referred to herein merely for ease of discussion, and that the systems and methods according to embodiments of the invention may be applied to any device used to image and/or inspect an interior portion of a cavity, such as a substantially tubular cavity, to significantly reduce or substantially eliminate angular geometric distortion. Further, although the term "IVUS system" refers to ultrasonic imaging systems, the systems and methods apply as well to other forms of intravascular imaging systems, such as, for example, those that use other forms of energy to make images. These systems may include, for example, optical imaging systems, such as, for example, Optical Coherence Tomography.

Figure 1A:
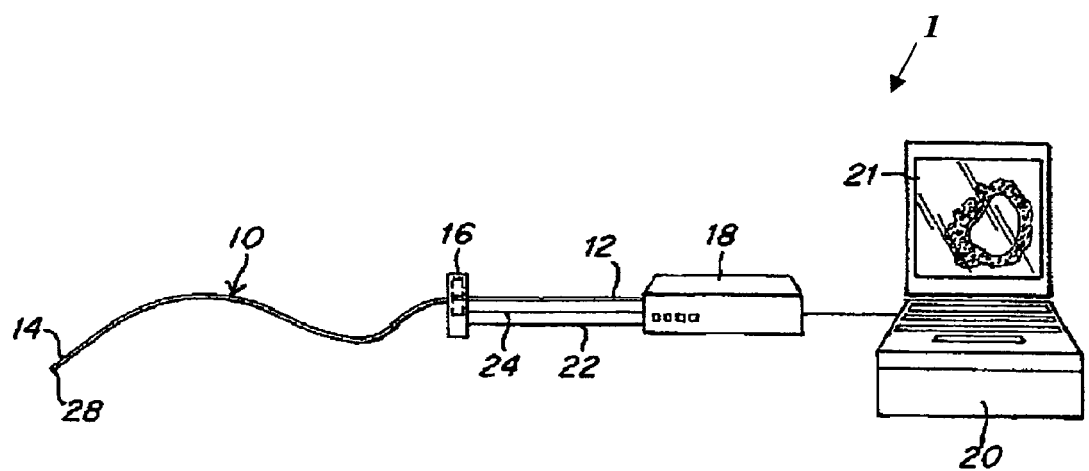
FIG. 1A is an exemplary IVUS imaging system by means of which embodiments of the invention may be implemented.

FIG. 1A illustrates an exemplary IVUS imaging system by means of which embodiments of the invention may be implemented. The system 1 of FIG. 1A includes a processor 20 which controls an electronics module 18. The electronics module 18 transmits an ultrasonic pulse to a transducer assembly 14 positioned at a distal tip 28 of a catheter 10 via data a path 12, and an angle encoder 16 records the relative angle of the catheter and transmits it back to the electronics module 18. Incremental angle information sensed by the angle encoder 16 is transmitted to the electronic module 18 via a data path, or cable 22, and a data path, or cable 24 provides the power and ground for the angle encoder 16. Echo data is returned to the electronics module 18 via the data the path 22, and the processor 20 accepts the echo digitized data from the electronics module 18 and stores it in a data table, such as the exemplary data table shown in FIG. 2. Software running in the processor 20, or alternatively, hardware or firmware running in the electronics module 18, manipulates the information in the data table to remove the NURD artifact and an intravascular image is then created by scan conversion of the information in the data table and displayed on a display module 21. In some embodiments of the invention, the processor 20 may be a separate unit, as shown in FIGS. 1A-1B, while in other embodiments of the invention, the capabilities of the processor 20 may be included in the electronics module 18.

Figure 1B:
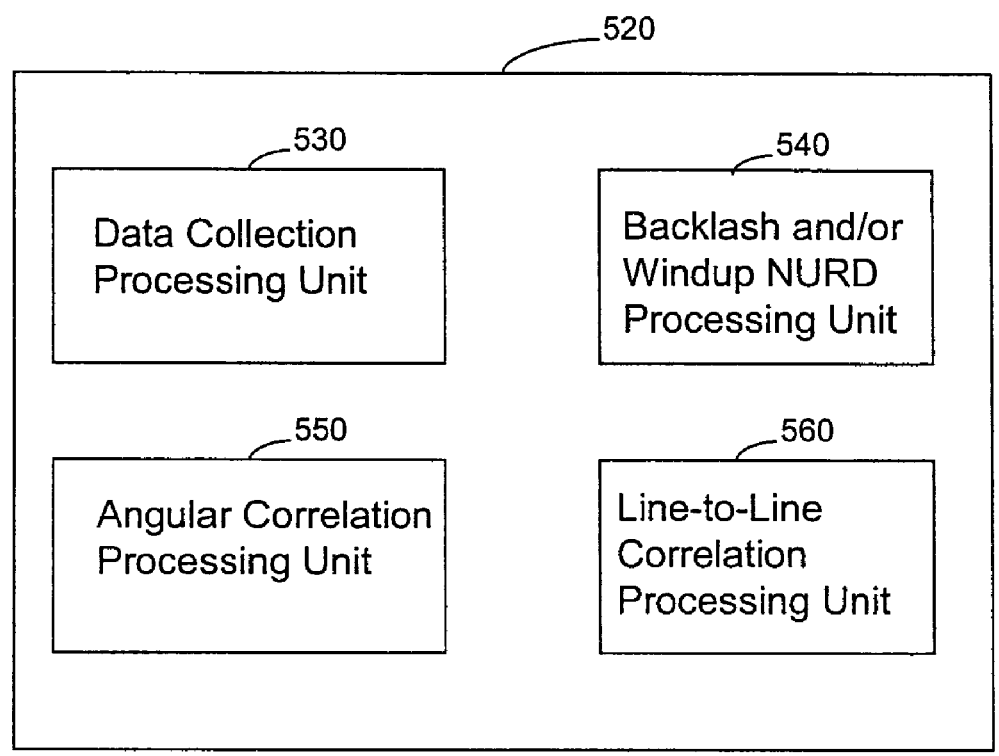
FIG. 1B is a block diagram of a processor according to an embodiment of the invention.

FIG. 1B is a block diagram of a processor in accordance with an embodiment of the invention. The processor 520 may be implemented, for example, by software provided in processor 20 of FIG. 1A or by hardware or firmware provided in electronics module 18 of FIG. 1A. The processor 520 of FIG. 1B includes a data collection processor unit 530 and one or more of a backlash and/or windup NURD removal processing unit 540, an angular correlation processor unit 550, and a line-to-line correlation processor unit 560. The processor units 540, 550, and 560 may all be provided and used as needed to significantly reduce and/or substantially eliminate NURD based on the application and/or the desired correction.

Alternatively, one or more of the processor units 540, 550, and 560 may be eliminated, for example, to reduce costs or processing time based on the application and/or the desired correction.

The data collection processor unit 530 functions to collect raw data, including angle and echo line data. The raw data may be stored in a data table, such as the exemplary table shown in FIG. 2 and further discussed below. For example, the data collection processor unit 530 may implement the methodology discussed below with respect to FIG. 4 of the present application. However, other data collection methodology may also be utilized.

The backlash and/or windup NURD removal processor unit 540 functions to remove NURD caused by backlash in the catheter when the direction of rotation is changed and a fixed amount of windup NURD is assumed to be present in a given imaging situation. For example, the backlash and/or windup NURD removal processor unit 540 may implement the methodology discussed below with respect to FIG. 5 of the present application. However, other methodologies capable of removing NURD caused by backlash in a catheter when the direction of the rotation is changed and a fixed amount of windup NURD is assumed to be present in a given imaging situation may be utilized.

The angular correlation processor unit 550 functions to remove backlash NURD by performing an angular correlation on the collected data. For example, the angular correlation processor unit 550 may implement the methodology discussed below with respect to FIG. 6 of the present application. However, other methodologies capable of removing backlash NURD by performing an angular correlation on the data collected may be utilized.

The line-to-line correlation processor unit 560 functions to calculate a cross-correlation between adjacent data lines and then discard redundant lines. For example, the line-to-line correlation processor unit 560 may implement the methodology discussed below with respect to FIG. 7 of the present application. However, other methodologies capable of calculating a cross-correlation between adjacent data lines and then discarding redundant lines of data may be utilized.

As discussed above, embodiments of the invention may be implemented using a plurality of processing steps in various combinations. Such plurality of processing steps or methods include collecting raw angle and echo line data, which may be stored in a data table, such as that shown in FIG. 2, removing backlash and/or windup NURD, performing angular correlation on the collected data and discarding redundant data, and performing line-to-line cross-correlation and discarding redundant lines of data. Each of these processing steps or processes will be discussed in more detail below. The processing steps may be used in various combinations to significantly reduce and/or substantially eliminate NURD, based on the application, for example, the particular imaging system utilized, and/or the desired correction. FIGS. 3A-3G show various exemplary combinations of the process steps, as discussed below.

Figure 3A:
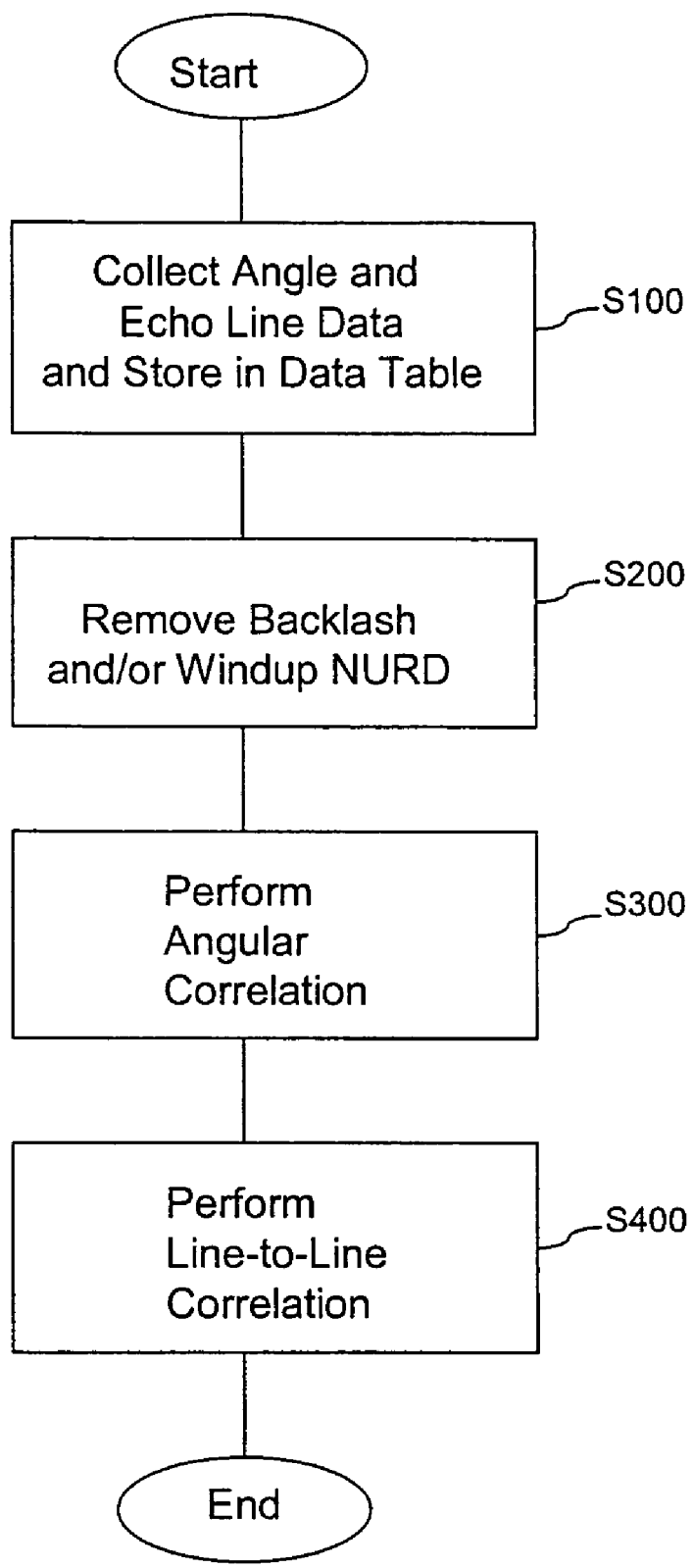
FIGS. 3A-3G are flow charts which show a number of different combinations and sequences of processing steps or methods which may be implemented in the exemplary IVUS imaging system shown in FIG. 1A and/or implemented by the processor shown in FIG. 1B.
Figure 3B:
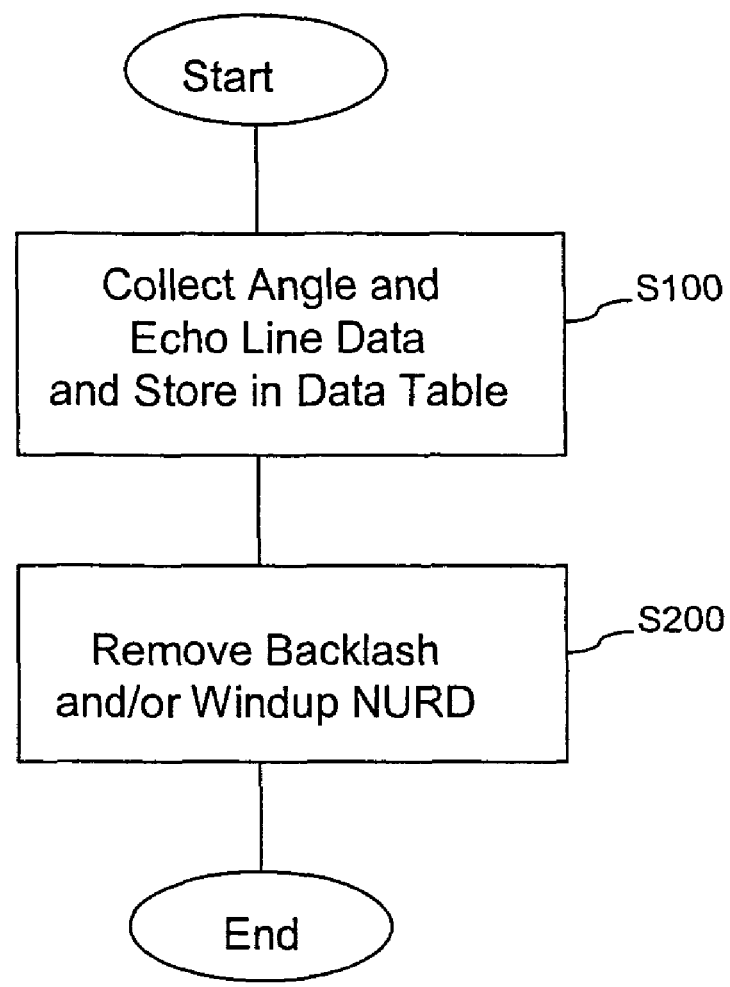
Figure 3C:
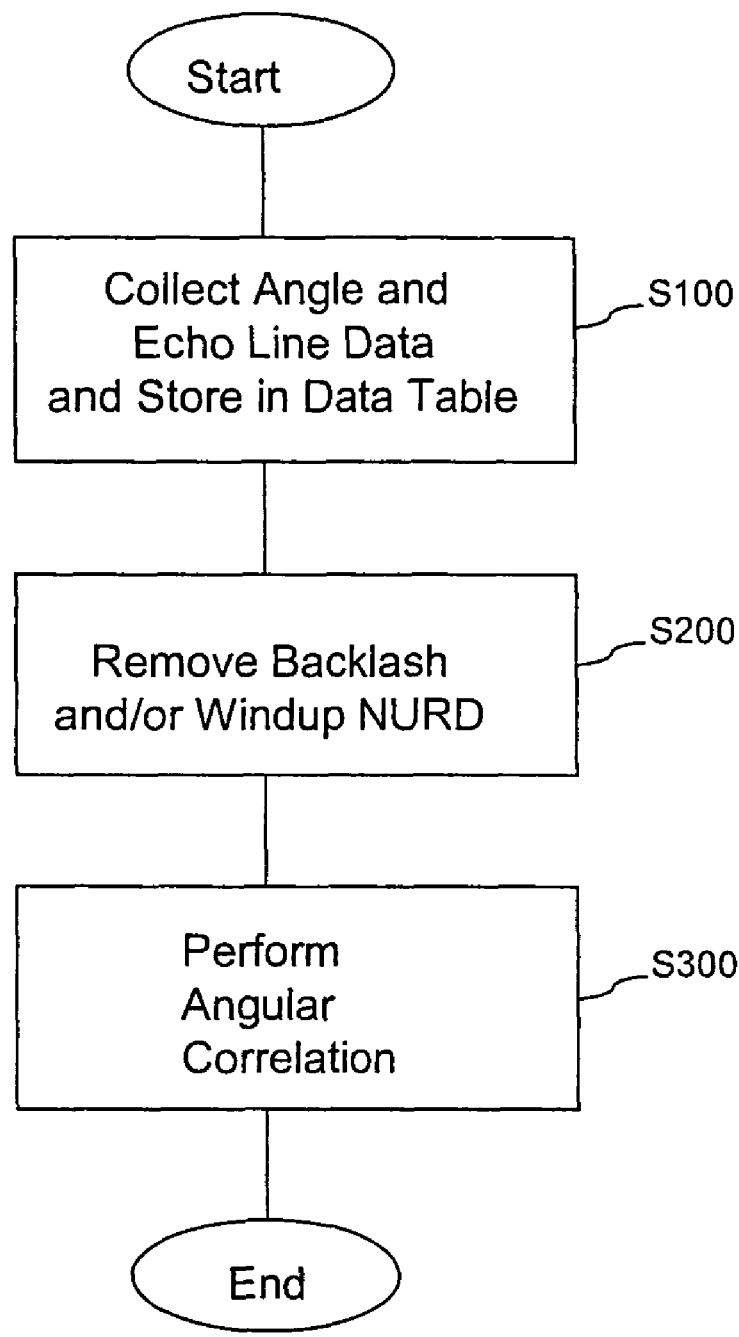
Figure 3D:
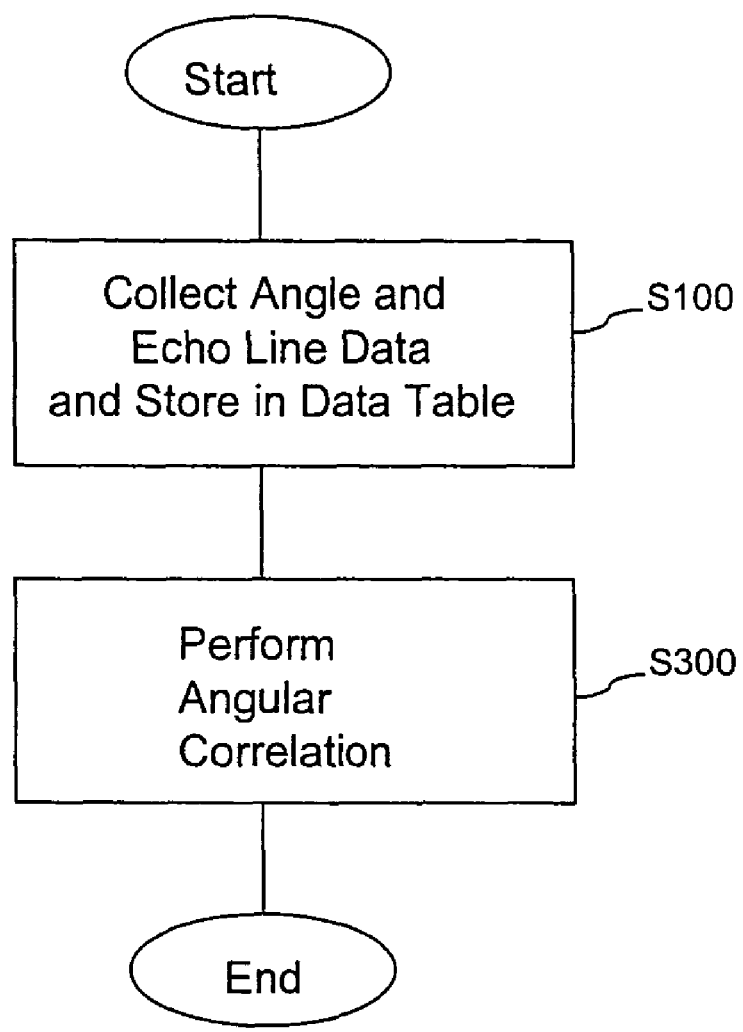
Figure 3E:
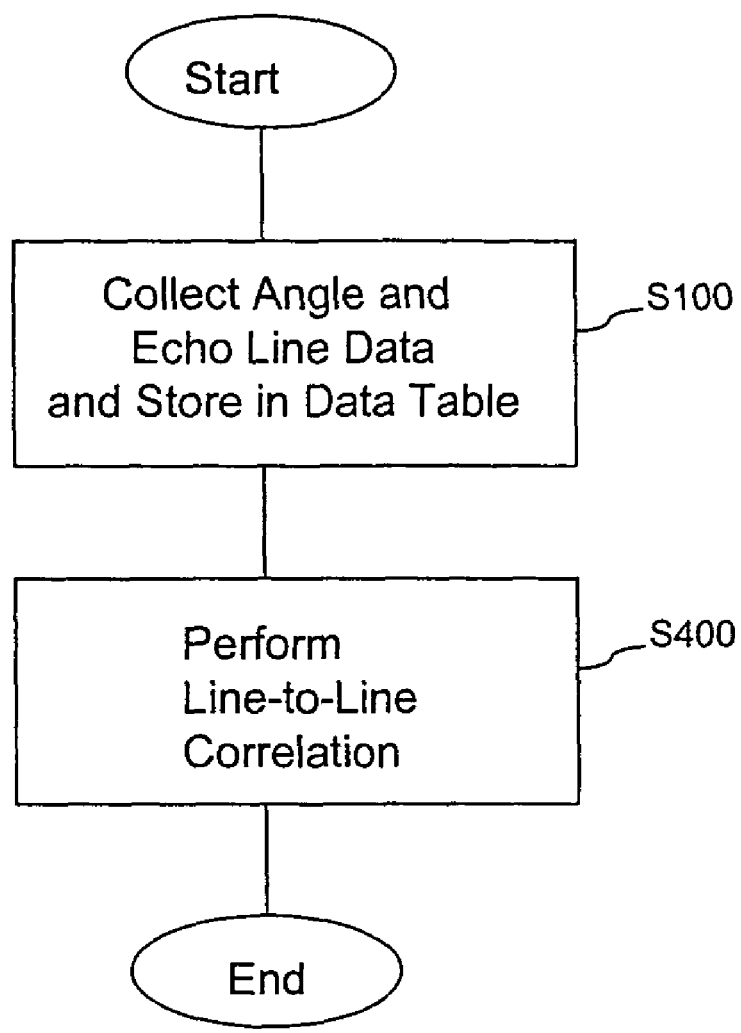
Figure 3F:
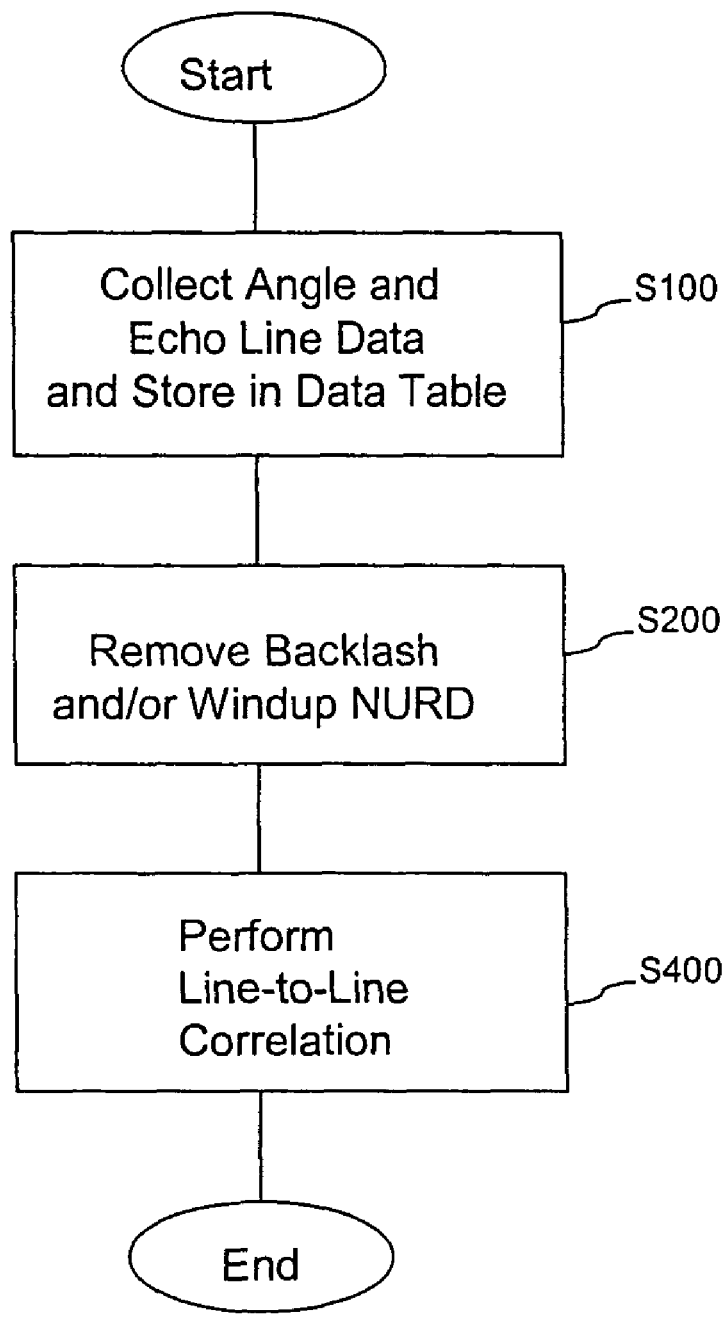
Figure 3G:
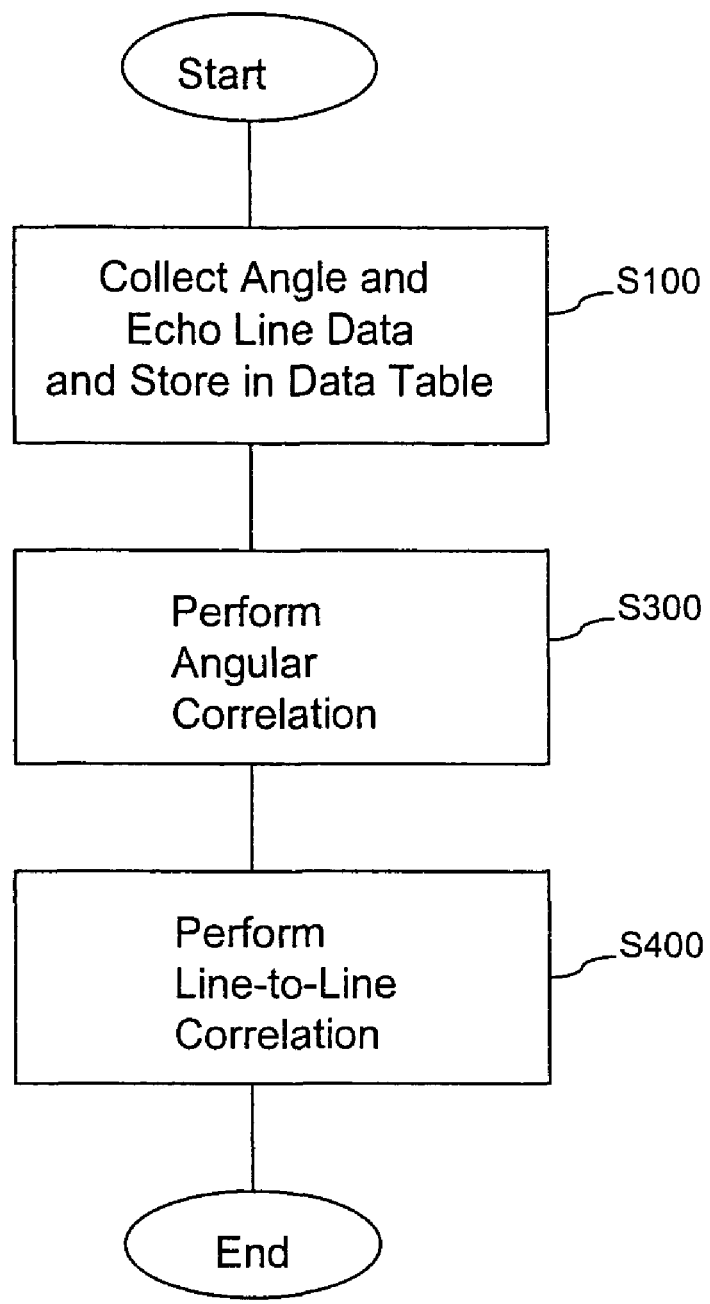

FIG. 3A is a flowchart of an exemplary arrangement of processing methods or steps in accordance with an embodiment of the invention. First, image data is collected in step S100 and then NURD is reduced through the removal of redundant data using known backlash data (S200), performing angular cross-correlation (S300), and performing line-to-line cross correlation (S400). Each of the NURD reducing processing steps can reduce NURD depending on the source of the NURD and the particular imaging system used. Further, each of the NURD reducing processing steps can also be used as standalone processing steps as necessary to, for example, reduce processing time and/or system cost. The steps which remove backlash/windup NURD (S200, S300) may be utilized with IVUS systems which change rotational direction, while the line-to-line correlation processing step (S400) may be applied to both unidirectional and bi-directional systems. Although the processing steps are all shown, sequentially, in FIG. 3A, any number of combinations and/or sequences, such as, for example, those illustrated in the flow charts shown in FIGS. 3B-3E, may be applied to significantly reduce and/or substantially eliminate NURD in an IVUS system, depending on the application or system used, and the desired correction or results.

The processing steps may be considered successive manipulations of information contained in a data table such as, for example, the data table shown in FIG. 2. In some IVUS systems, a line rate, or data collection rate, is fixed, while the number of lines in an image is variable, and the number of lines then depends on a somewhat variable catheter rotation rate. Consequently, the number of lines in a data table for such a system is also variable. In contrast, in other IVUS systems, the number of acoustic lines is fixed, and the line rate varies based on an angular velocity of the catheter. The processing steps can be applied to either type of IVUS system in a number of different ways, including, for example, a software algorithm, firmware controlling a Field Programmable Gate Array (FPGA), an Application Specific Integrated Circuit (ASIC), a pipeline processor implemented totally in hardware, or a combination of one or more of these.

Each of the processing steps will now be discussed in more detail.

Figure 4:
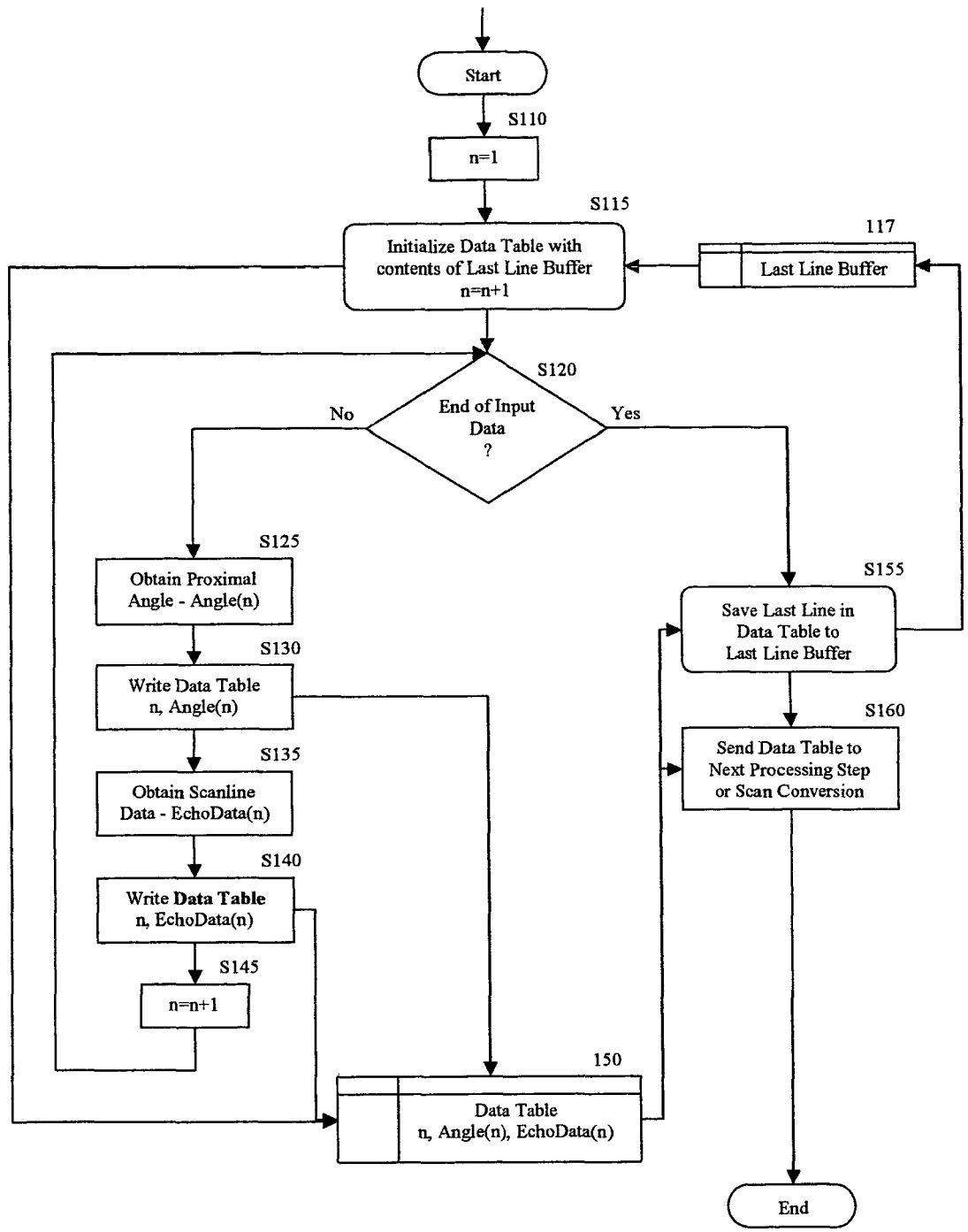
FIG. 4 is a flow chart of a process to collect raw angle and echo line data such as that shown in FIG. 2, in accordance with an embodiment of the invention.

FIG. 4 is a flow chart of the data collection processing step or method (S100) shown in FIGS. 3A-3G. The data collection processing step simply collects angle and echo line data. The data may be stored in a data table, such the exemplary data table 50 shown in FIG. 2. The length of the data table may be established based on the amount of memory available. Further, the data table may contain all of the acoustic echo lines from a few revolutions of a catheter in a motor driven, unidirectional IVUS system, or 10 to 15 direction reversals in a manually rotated, bi-directional IVUS system. The data collection processing step builds the initial raw data table of angles and associated image lines. It is well understood that the line data that represents the returned echoes from a constantly increasing radius or depth is, in fact, an array. However, for ease of discussion, each line of information will be treated as if it is a simple scalar rather than an array.

Referring again to FIG. 1A, ultrasound scanning is initiated by electronics module 18 with the transmission of a pulse of sound to the transducer assembly 14. Echoes are returned to the transducer assembly 14 from the acoustic impedance discontinuities encountered by the pulse in the tissue being interrogated, and are processed into a time series of discrete samples. This can be accomplished in a number of ways, including, for example, by digitizing the returning radio frequency signal directly, or by mixing it down to an intermediate or baseband frequency, or by detecting the information and digitizing the detected signal. In any case, the sampling rate is preferably consistent with the Nyquist criteria of at least twice the bandwidth of the signal to be sampled. It is preferable to digitize the detected data to minimize the number of sampled points in an echo line.

For example, for a ~40 MHz center frequency transducer with a ~60% fractional bandwidth, the information bandwidth of the amplitude modulated signal is ~24 MHz. According to the Nyquist criteria, this signal must be sampled at least ~48 million times each second. If, for example, a ~50 MHz sampling rate is used, and it is desired to collect an echo line of ~10 mm in length, then the number of samples in the echo line is:

$$EchoLineSamples = \frac{Line\ Length * SamplingRate}{(Speed\ of\ Sound\ in\ Water/2)} \quad \text{(Eqn. 1)}$$

$$= \frac{10\ mm * 48\ samples/\mu sec}{1.5\ mm/\mu sec / 2}$$

$$= 623\ samples$$

The number 2 in the denominator of Equation 1 reflects the fact that the sound must travel to the point of interest, and the echo must return from that point to the transducer, effectively progressing at half the speed of sound in the tissue. Along with the echo data, the proximal angle for each scan line at the time of pulse transmission is recorded by the electronics module 18.

Each time the data collection processing step is invoked, incoming pairs of proximal angle and echo data are used to construct a new version of the data table. As previously discussed, the data table may contain a list of angles and the echo data that is captured at each particular angle. For ease of discussion, the exemplary data table shown in FIG. 2 is represented as an array with three columns and "N" rows. The first column serves as an array index "n" which is an ordered integer from 1 to "N" where "N" is the number of rows (i.e. proximal angle/scan line pairs) obtained. The second column is the Angle(n) and the third column is the EchoData(n,t). Each entry in the EchoData column is a time series or array of discrete samples. The time values start from the moment the transmit pulse occurs until the last echo of interest is returned from the maximum depth to be displayed in the image. These time values correspond linearly with distance or depth from the face of the transducer.

The number of rows "N" in the data table may be a function of a number of design considerations. In general, a shorter data table results in a shorter overall latency period through all of the processing steps. Input data sets as short as one proximal angle/echo data pair are allowed. This yields a data table size of N=2 due to the optional buffering of the last line from one iteration of the data collection processing step to the next; this configuration supports pipelined operation in which data flows continuously through all processing steps. The determination of the end-of-input-data condition includes, but is not limited to, the following conditions:

1. A predetermined number of scan lines have been received (1 . . . N).
2. A predetermined number of complete 360° image frames have been received (1 . . . F).
3. A predetermined time interval has elapsed.
4. A predetermined number of direction reversals have occurred (1 . . . R).
5. A predetermined time of no input activity has occurred.

As shown in FIG. 4, a line counter is initially set to 1, in step S110, and the counter is increased by 1, in step S115, as the data is collected and stored. The method determines if the end of input data has been reached, in step S120, based on the criteria set forth above. If the end of input data has been reached, the last line in the data table 150 is saved to the last line buffer 117, in step S155, and the data table 150 is sent to the next processing step, or for scan conversion, as appropriate, in step S160. If the end of input data has not been reached, the proximal angle(n) is obtained, in step S125, and written to the data table 150, in step S130, and scan line echo data(n) is obtained, in step S135, and written to the data table 150, in step S145. The counter is then increased by 1, in step S145, and the process repeats until the end of input data is reached, in step S120.

Figure 5:
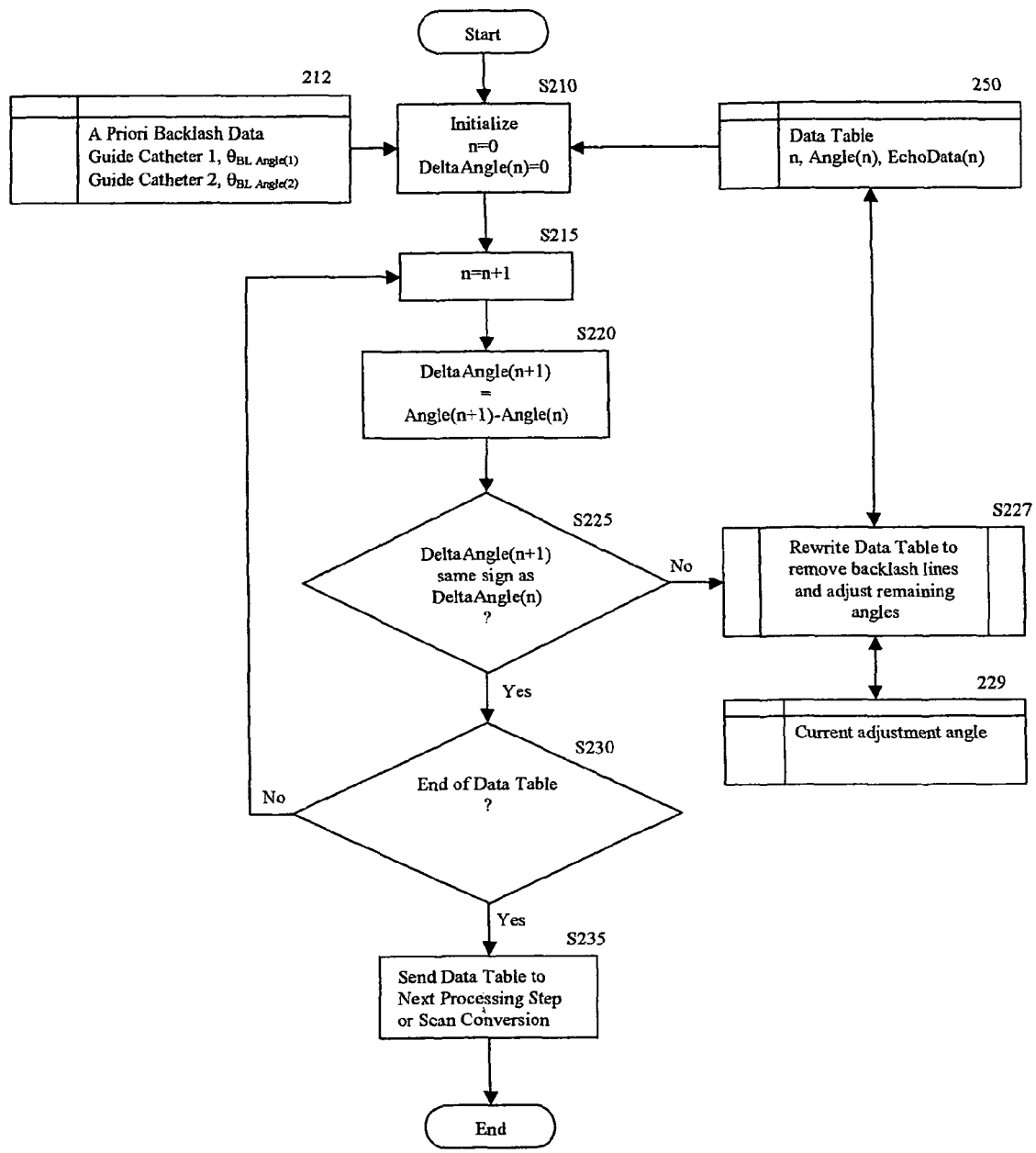
FIG. 5 is a flow chart of a backlash and/or windup NURD removal process, in accordance with an embodiment of the invention.

FIG. 5 is a flow chart of the backlash and/or windup NURD processing step or method shown in FIGS. 3A-3C and 3F. This processing step senses when the catheter has reversed its rotational direction, and removes the lines corresponding to a predetermined minimum backlash angle from the data table. The remaining lines are then rotated by the predetermined backlash angle to remove the angular distortion. An estimate of the minimum amount of backlash that will always occur upon a change of rotational direction for any particular imaging situation is predetermined and loaded into an a priori backlash data table. Many factors influence these backlash angles, including, for example, the type of guide catheter used, the access site to the patient, the guidewire employed, a patient body type, and other such factors which have had their minimum backlash angles experimentally measured for each of the catheters that may be compatible with a particular imaging system being used. This processing step can be used with a catheter that can image while being rotated in both directions, i.e., a bi-directional IVUS system.

When the rotational direction is reversed, the distal tip of the transducer is assumed to be stationary until the minimum backlash angle has passed at the proximal end of the catheter. The backlash angle is, for purposes of discussion, assumed to be the total angle necessary to unwind any twist in the catheter added to the angle necessary to rewind the catheter in the opposite direction so as to start the distal tip moving again in the opposite direction. After the proximal end of the catheter has exceeded the backlash angle, the method begins writing lines according to the incremental angles measured at the proximal end. Conceptually, the best case backlash scenario occurs when the catheter is held as straight as possible with no bends other than those created by the guide catheter. All other scenarios will typically have more backlash since, in general, more friction will be present due to the catheter being forced to bend by contact with the vessel wall. Since guide catheters of various shapes are typically used with IVUS imaging systems, putting the IVUS catheter inside the guide catheter and measuring the backlash when there is no load on the part of the catheter that extends distal to the tip of the guide catheter, or the part that is proximal to the proximal end of the guide catheter, will be a reasonable best case minimum backlash measure.

As discussed above, the backlash/windup NURD removal processing step or method acts to remove NURD caused by backlash in the catheter when the direction of rotation is changed. This fixed amount of windup NURD is assumed to be present in a given imaging situation. The a priori backlash data table may provide measured, estimated, or calculated backlash data for a variety of combinations of guide catheter-IVUS catheter combinations, and allows this processing step to significantly or completely remove the minimum amount of NURD that will always occur for any one of the combinations available.

In the method of FIG. 5, the a priori backlash data table 212 and the data table 250 are made accessible as the method is initialized, in step S210, and a processing loop is entered where the lines in the data table 250 are examined, in steps S215, S220. A rotational direction change is identified, in step S225, when the catheter angles in the data table 250 go from monotonically increasing to monotonically decreasing, or vice-versa. If no direction change has occurred, no change to the data table 250 is made, and the next angle in the data table 250 is examined, in step S215, until the end of the data table 250 is reached, in step S230.

However, when a direction change has occurred, in step S225, the data table 250 is rewritten to remove all of the angles and echo data lines that are contained within a preset backlash angle, in step S227. All of the data table 250 entries in the intervening backlash angle are removed, and the angles for all subsequent rows in the data table 250 are adjusted, in step S227, by subtracting or adding the preset backlash angle from the a priori backlash data table 212, plus the current adjustment angle 229 from the original angle depending on whether the direction change was from clockwise to counterclockwise, or from counterclockwise to clockwise.

Referring again to the system shown in FIG. 1A as an example, this assumes that the transducer assembly 14 at the distal end 28 of the catheter 10 will be stationary after the change in direction, but before the complete backlash angle has been subtended, so echo data for all of the lines in the intervening backlash angle will be nearly identical. The backlash/windup removal processing step is computationally very simple and its implementation is inexpensive either from a parts cost or a computer processing time perspective. As such, it could eliminate the backlash lines without the expense of the additional computer cycles required for the angular or line-to-line correlation steps. If the line-to-line correlation processing step or the angular correlation processing step is employed in addition to the backlash/windup removal processing step, then it is preferable that the backlash/windup removal processing step precede either or both of the other two steps. More particularly, the line-to-line correlation step and the angular correlation step will remove the redundant lines in the backlash angle because they will be highly correlated. The backlash/windup removal processing step would then simply sense the change in direction and remove an additional set of lines that would in fact be valid data that is not redundant. It can, however, be desirable to have the backlash removal processing step employed in conjunction with the other processing steps because it is a more efficient way to remove that backlash artifact, thereby saving computer cycles for other things, such as, for example, scan converting the acoustic lines into images, monitoring and responding to the human interface, and any signal processing tasks that the system employs.

After all of the rows in the incoming data table have been processed, in step S230, the modified data table can be sent to the next processing step for further NURD reduction, or sent to be scan converted and displayed, in step S235. The current adjustment angle 229 is updated by adding or subtracting the backlash angle and retained for the next invocation of the backlash/windup NURD removal processing step.

Figure 6:
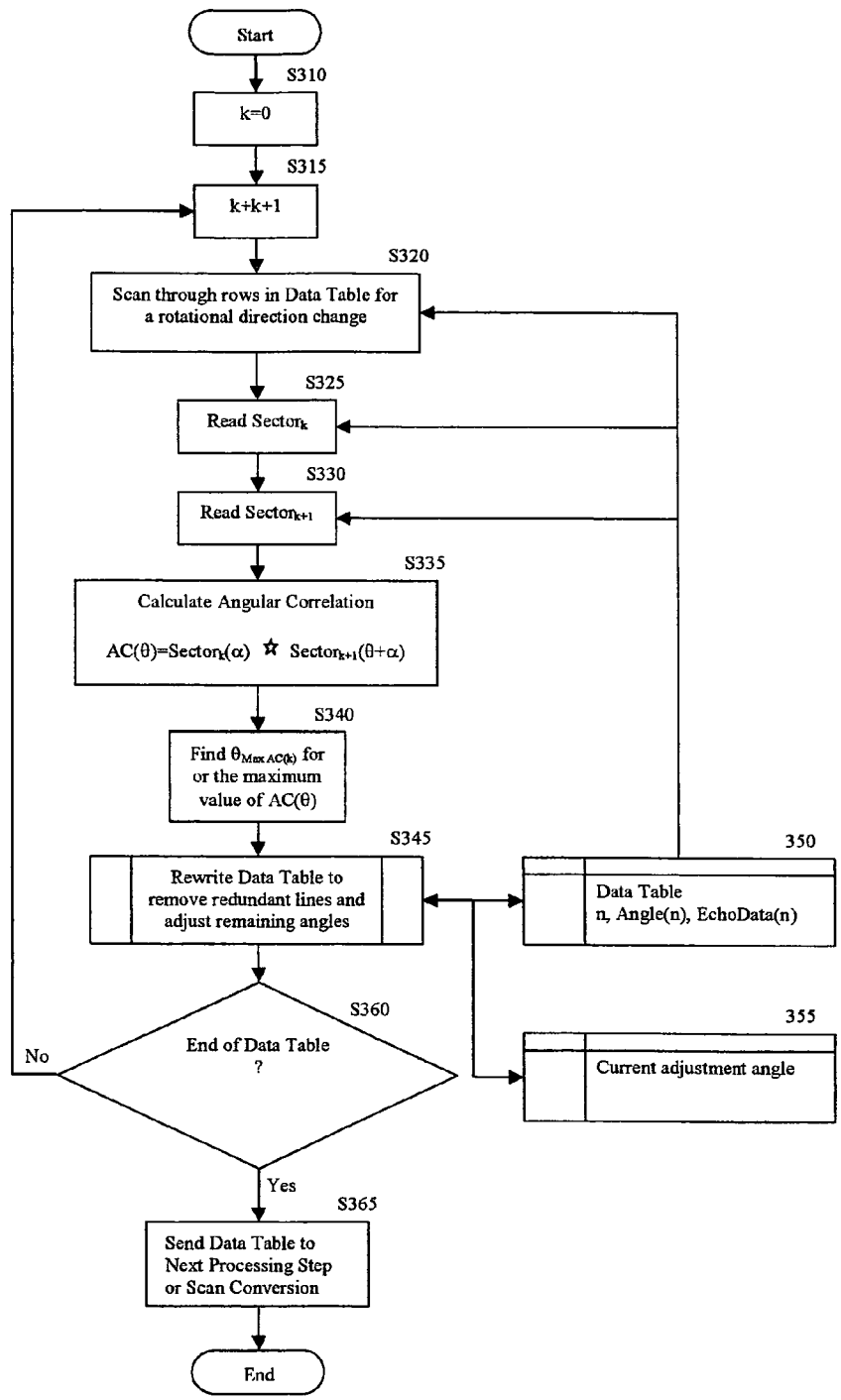
FIG. 6 is a flow chart of an angular correlation process, in accordance with an embodiment of the invention.

FIG. 6 is a flow chart of the angular correlation processing step or method shown in FIGS. 3A, 3C-3D, and 3G. Like the backlash/windup NURD removal processing step, this processing step senses a reversal in the direction of rotation. The process then calculates an angular cross-correlation between sectors that occur before and after the direction change. This may be, for example, complete 360-degree images, or sectors of images, and the same processing step may be applied when changing from clockwise to counterclockwise rotation as when changing from counterclockwise to clockwise rotation. The angle that produces the maximum of the angular cross-correlation is used to rotate the image sector so as to properly align the two images sectors without the intervening backlash. In this case, angle values in the data table are shifted by the angle that corresponds to the maximum cross-correlation angle, while the echo data remains unchanged.

The angular correlation processing step may follow the backlash/windup NURD removal processing step, or may be used immediately following the data collection processing step. When used subsequent to the backlash/windup NURD removal processing step, the angular correlation processing step removes any remaining backlash that occurs in addition to the minimum that was stored in the a priori backlash data table. This additional backlash angle is a consequence of the less than ideal circumstances that were measured, estimated, or calculated in the a priori backlash data table. For example, higher catheter rotation velocity, more total bending of the catheter as it accesses the desired vasculature, and contact with the vessel walls after exiting the guide catheter all cause more frictional drag and, consequently, more backlash. The angular correlation processing step may be carried out on the raw data in the data table, or the acoustic lines can be moved to the nearest display line and the intervening pixels left uncalculated As set forth above, the angular correlation processing step aligns the sectors of an image just prior to and subsequent to a change in catheter rotation direction. As shown in FIG. 6, a loop index "k" is initially set to zero, in step S310, the loop index "k" is incremented for each change in catheter rotation direction, in step S315, and a rotational direction change is detected, in step S320, as discussed in more detail with respect to FIG. 8A. Once the direction changes are located in the data table 350, Sector$_k$, which represents the set of rows that represent the image information a set amount before the change in direction and Sector$_{k+1}$ which represents the image information a set amount after the change in direction can be determined, in steps S320, S325, and S330. For ease of discussion, forty degrees is chosen as the set amount, as a 40 degree sector angle would provide sufficient image area to provide a robust angular cross-correlation but is small enough so that an operator who may be manually sweeping out the image would sweep through the entire sector angle in normal practice; however, other sector angles may also be appropriate. This corresponds to the numerical integration from −20 degrees to +20 degrees in Eqn. 2. This angle can be a predetermined number stored in a table much like the a priori backlash data table discussed above, and may represent an optimum angle depending on any particular imaging situation that can be known in advance.

The 40 degree sector just prior to a catheter rotational direction change is compared to the 40 degree sector subsequent to the direction change, and the rotation angle necessary to align these two sectors is calculated, in step S335, based on an angular cross-correlation formula shown below in Equation 2. Preferably, the angular cross correlation is performed on the "pre-scan-converted" lines in the data table with the angular position of the acoustic lines rounded to the nearest display line. Once the angular cross-correlation has been calculated, in step S335, the actual angles are used for scan conversion purposes.

$$AC_k(\theta) = Sector_k(\theta) \star Sector_{k+1}(\theta) \qquad \text{(Eqn. 2)}$$

$$AC_k(\theta) = \sum_{\alpha=-20}^{20} Sector_k(\alpha) \times Sector_{k+1}(\alpha - \theta)$$

Where: $AC_k(\theta)$ is the Angular Correlation as a function of the offset angle $\theta$, the angle $\theta$ is allowed to vary over + and −20 degrees, and $\alpha$ is the angular index over which the correlation is integrated.

It will be obvious to one skilled in the art that this calculation is in fact a summation over as much as 80 degrees of image data.

The angular cross-correlation function in Equation 2 will have a maximum value $\theta_{MaxAC(k)}$ for the angular rotation ($\theta$) that best aligns the two sectors of the IVUS image. Once the angular cross-correlation is calculated, in step S335, the maximum of the function is determined, in step S340, Sector$_{k+1}$ is rotated by that angle, and the data table 350 is rewritten to remove redundant lines and adjust the remaining angles, in step S345. The rotation of the sector involves only the addition of the $\theta_{MaxAC(k)}$ value, plus the current adjustment angle 355, to the Angle(n) column for the EchoData(n) line that marks the beginning of Sector$_{k+1}$ through the end of the data table 350.

Once the angles in the data table 350 have been rewritten, in step S345, if the end of the data table 350 has not been reached, in step S360, the loop index "k" is incremented, in step S315, the next change in direction is found, in step S320, and the process repeats until the last direction change has been processed. When the last direction change has been processed, the data table 350 is ready to be sent to the next processing step or scan-converted and displayed, in step S365. The current adjustment angle 355 is updated by adding in the net sum of all the $\theta_{Max\,AC}$ for all the sectors in the data table and retained for the next invocation of this processing step.

Figure 7:
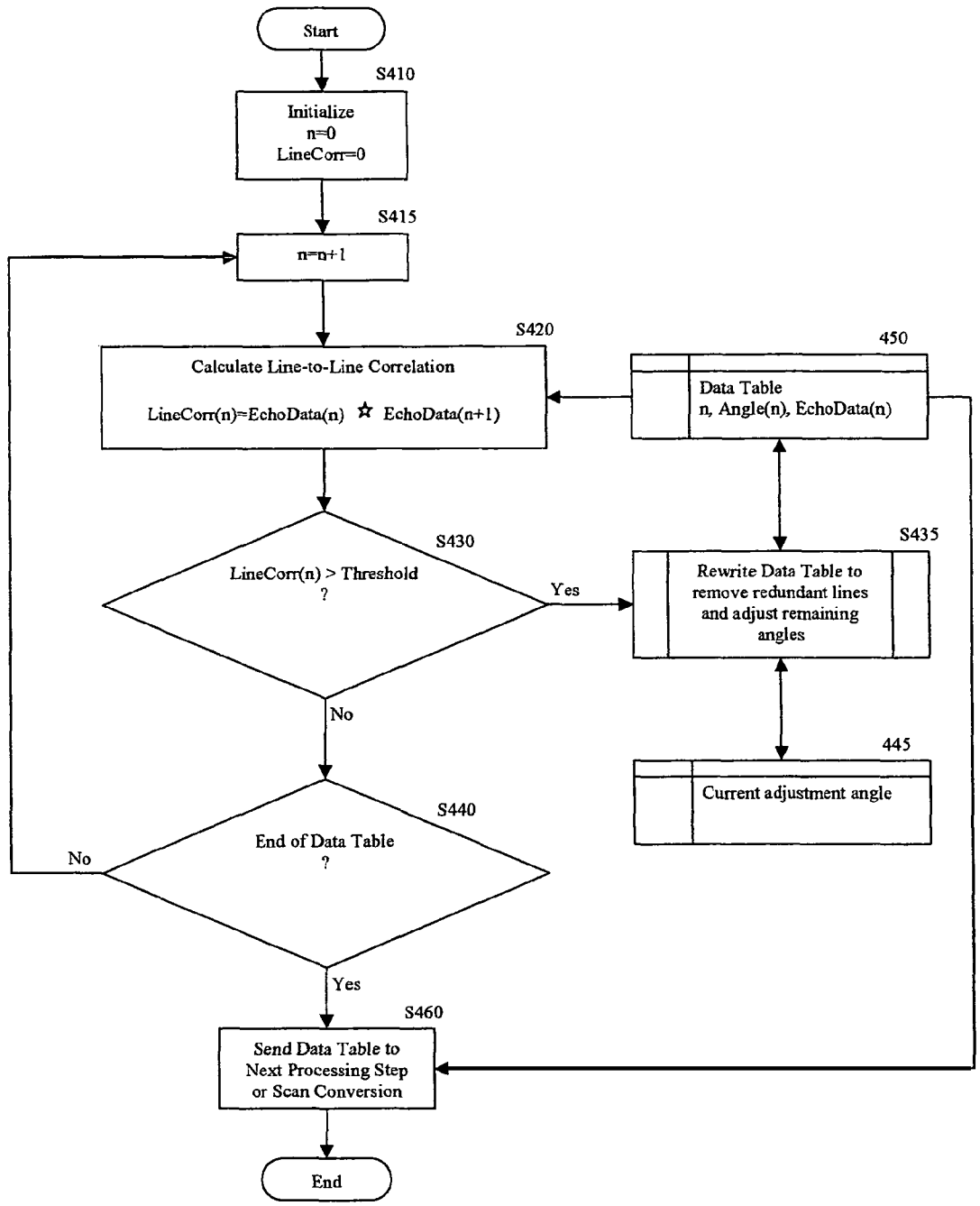
FIG. 7 is a flow chart of a line-to-line correlation process, in accordance with an embodiment of the invention.

FIG. 7 is a flow chart of the line-to-line correlation processing step or method shown in FIGS. 3A and 3E-3G. This processing step is applicable whether the catheter is unidirectional or bi-directional, and is used to calculate a cross-correlation between adjacent lines. If the cross-correlation is above a preset threshold, it is assumed that the distal end of the transducer assembly is substantially stationary, that the lines are taken from the same angular location, and therefore one of them is redundant and should be discarded. This is considered to be a NURD sector of the IVUS image, and would likely show up as a "streaked" sector where the lines have the same echo pattern for many different apparent angles. Thus, all but the first or last line are discarded until the correlation coefficient drops below the preset threshold. A reduction in the cross-correlation indicates that the transducer is again rotating and presumably tracking the proximal angle encoder values, and the image lines are written accordingly. With a frame buffer and sufficient line density, the changing lines at either edge of the sector which would have been "streaked" (i.e. the NURD sector) can be repositioned across the (to be discarded) highly correlated sector to reduce the geometric distortion.

This processing step can assume that the transducer is moving at a constant velocity when the line-to-line correlation coefficients are no longer approximately one. Further, it may be assumed that the transducer will accelerate before reaching a certain velocity that it will maintain until either the drive on the proximal end is changed or the line-to-line correlation again approaches one. Similarly, for the lines just preceding the NURD sector where the lines are highly correlated, it may be assumed that the transducer decelerates to zero angular velocity at the edge of the leading edge of the NURD sector. Either of these corrections allows a more accurate geometric presentation of the received data than the constant velocity assumption that is implicit in conventional mechanically rotated IVUS systems.

The line-to-line correlation processing step may accept the raw data table from the data collection processing step, and/or may accept the data table as processed in either the backlash/windup NURD reduction processing step and/or the angular correlation processing step. The method is initialized, in step S410, and the line number in the data table 450 is incremented, in step S415. A correlation between adjacent lines is calculated, in step S420. The LineCorr(n) is compared to a predetermined threshold (Th$_o$), in step S430, and if the LineCorr(n) is greater than the predetermined threshold (Th$_o$), these highly correlated lines are discarded and the remaining lines are reoriented, in step S435. The process is repeated until the end of the data table 450 is reached, in step S440, and the data table 450 is ready for scan conversion and/or display, in step S460. The formula for the line-to-line correlation calculation, in step S420, is shown in Equation 3.

$$LineCorr(n) = EchoData(n, i) \stackrel{\star}{\approx} EchoData(n+1, i) \quad \text{(Eqn. 3)}$$
$$= \frac{1}{(EchoLineSamples - 1)} \times \sum_{i=1}^{EchoLineSamples} EchoData(n, i) \times EchoData(n+1, i)$$

This correlation value would typically be between 0.90 and 1.00 if the two lines were received while the transducer, at the distal end of the catheter, was in substantially the same position. However, it is not exactly 1.00, because there is always some level of thermal noise in the receiver and the transducer is never perfectly stationary in a living system due to respiration, heart beat, patient motion, and other such external influences. If the line-to-line correlation coefficient is low, then the adjacent acoustic lines represent substantially independent acoustic lines. Equation 3 can be implemented on the EchoData signals after the DC component has been removed (AC coupled) or with the DC component intact with similar results.

The correlation coefficient, LineCorr(n), for the n$^{th}$ acoustic line and the n+1$^{st}$ acoustic line is then compared to a preset threshold value (Th$_o$) of, for example, 0.95, in step S430. If the correlation between the lines exceeds the preset threshold (Th$_o$), then it is assumed that the transducer is not moving during the time the two lines were acquired, one of the lines is discarded, and the data table 450 is rewritten accordingly, in step S435. The process of re-writing the data table 450 is discussed in more detail with respect to FIGS. 8A-8B. If the correlation between the lines is less than the preset threshold (Th$_o$), in step S430, then the lines are assumed to be valid lines, substantially without NURD, and the next pair of lines is examined. When all of the lines in data table 450 have been processed, in step S440, the data table 450 may be sent to another processing step, or scan-converted and displayed, in step S460. The current adjustment angle 445 is updated, by adding in the net angle of image sector data removed and angle of the image sector data retained for the next invocation of this processing step.

Figure 8A:
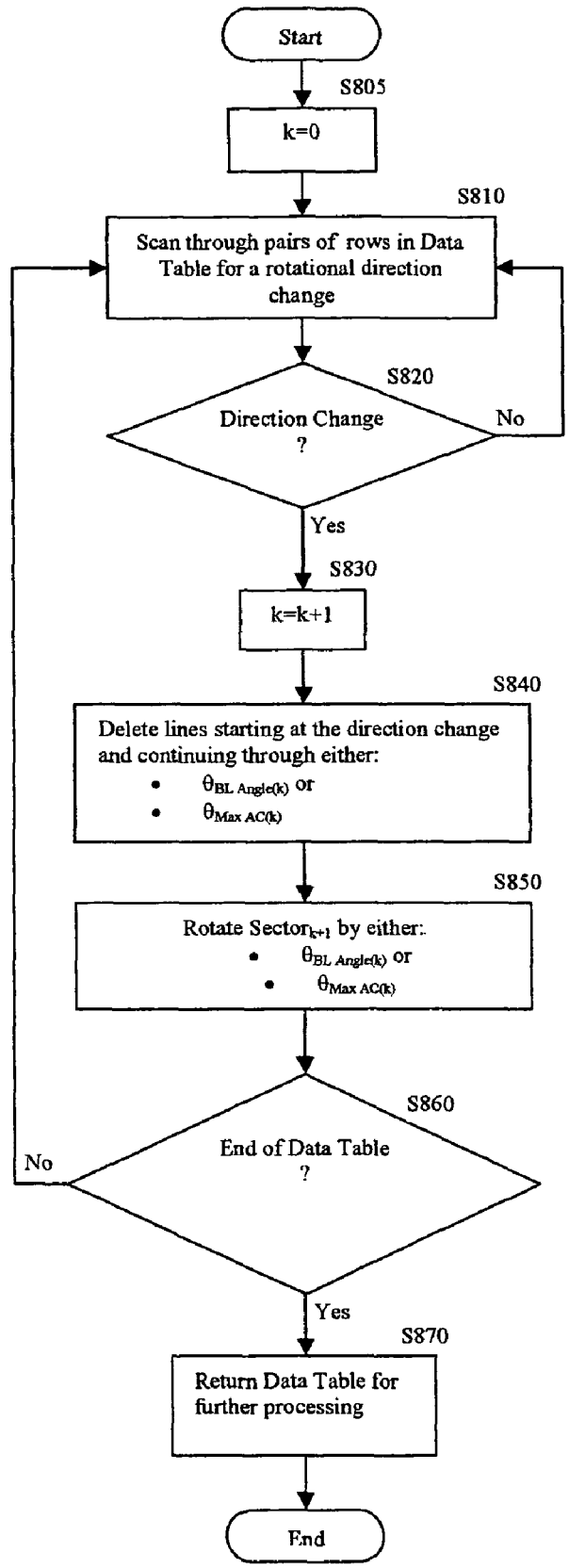
FIG. 8A is a flow chart of a data table rewriting process, in accordance with an embodiment of the invention.
Figure 8B:
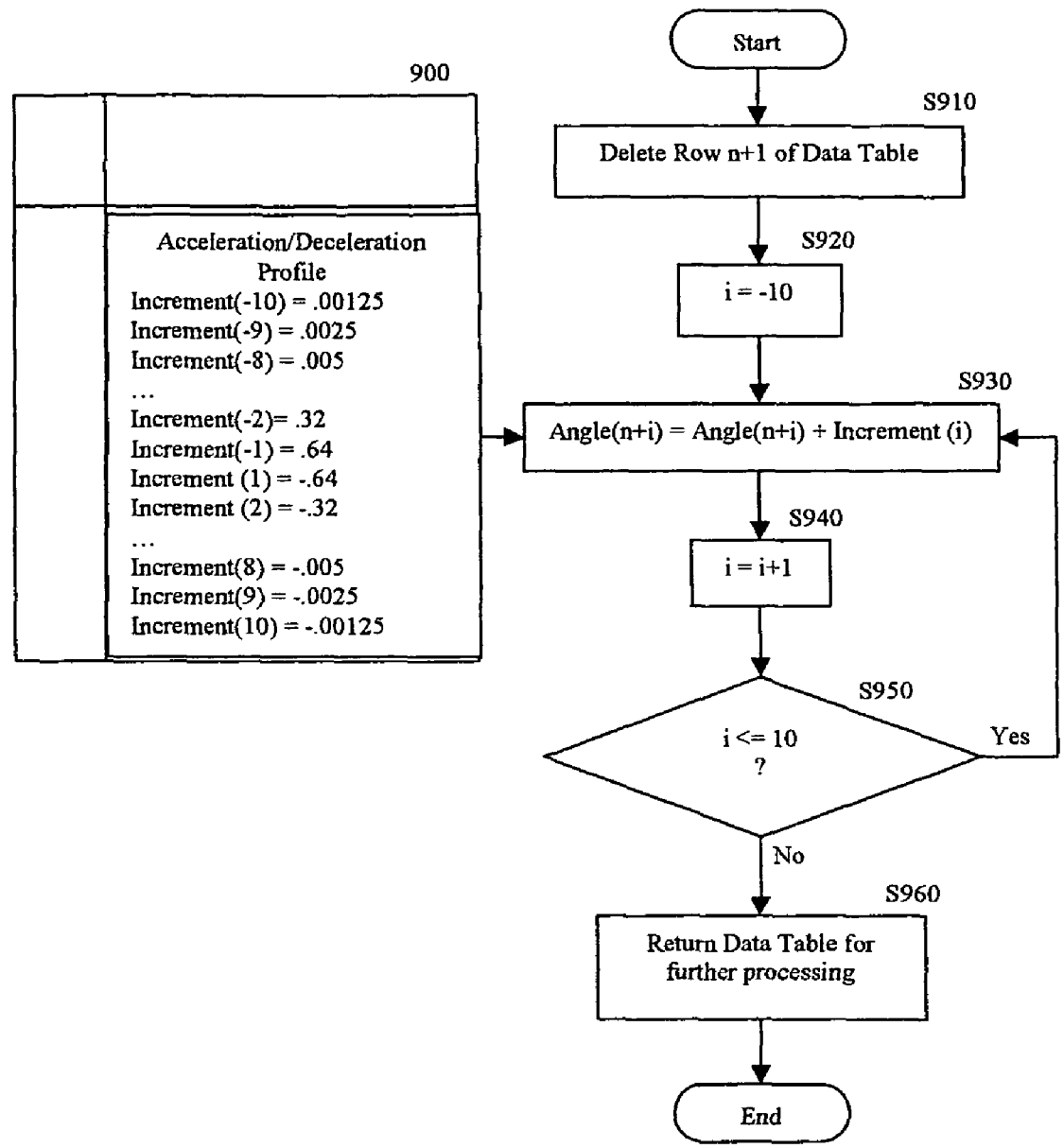
FIG. 8B is a flow chart of a data table rewriting process, in accordance with an embodiment of the invention.

FIGS. 8A-8B are flow charts illustrating data table rewriting processes. The basic difference in these two processes is in the assumptions that are made for the correct replacement of remaining lines after aberrant lines have been removed. In the event of NURD caused by backlash during a direction reversal, it is assumed that the distal tip of the catheter was stationary during the backlash angle. Once the backlash angle is exceeded, the distal tip moves at the same angular velocity as the proximal end of the catheter, thus causing the sector of image that occurs after the change in rotational direction to be discarded as the catheter traverses the backlash angle, and the remaining angles in the sector to be adjusted to rotate the image accordingly.

In contrast, when there is no change in rotational direction, it is assumed that the distal tip of the catheter decelerates just prior to the occurrence of NURD, remains substantially stopped during the NURD sector, and accelerates just subsequent to the NURD sector. Although, for ease of discussion, it is assumed that the deceleration and acceleration are approximately of the same magnitude and duration, this is not a necessary condition, as the acceleration and deceleration profiles may be stored in a table, and may reflect any profile that the actual catheter is likely to experience. In this situation, the remaining lines may be repositioned prior and subsequent to the NURD sector to fill in the gap of discarded lines, and subsequent data tables will have their initial angle adjusted to reflect the cumulative angles and lines removed from previous versions of the data table. This cumulative angle adjustment from sector to sector, or from data table to data table, is referred to as current adjustment angle.

FIG. 8A is a flow chart illustrating a data table rewriting process invoked by either of the backlash/windup NURD removal processing step or the angular correlation processing step. The direction change counter "k" is initialized, in step S805, and angles for pairs of adjacent lines are examined, in step S810, to determine if the rotational direction has changed, in step S820. If not, the search for a change in direction continues as step S810 is repeated. If a direction change is found, in step S820, the index "k" is incremented, in step S830, and the NURD lines are deleted according to the algorithm in either the backlash/windup NURD removal processing step or the angular correlation processing step, in step S840. The sector is then rotated again by an angle specified in the appropriate algorithm, in step S850. This process continues until the entire data table has been processed, in step S860, and the data table is returned to the appropriate processing step, in step S870.

FIG. 8B is a flow chart illustrating a data table rewriting process invoked by in the line-to-line correlation processing step when there is no change in rotational direction. This process requires a pre-calculated table which dictates how valid lines are to be repositioned to cover a gap left behind by redundant lines, referred to as the acceleration/deceleration profile 900. If the NURD sector is relatively wide, then the acceleration and deceleration may be spread over a wider sector of good data. However, if the NURD occurs in only a few lines, then the acceleration and deceleration of the catheter most likely occurs over only a few adjacent lines before a constant angular velocity is restored. The algorithm may include an accumulator to count the total number of adjacent lines with high correlation coefficients and then choose an appropriate acceleration/deceleration profile from a two-dimensional data set that varies each as a function of the number of lines to be discarded. However, for ease of discussion, a simple one-dimensional table is shown in FIG. 8B.

The method of FIG. 8B is initiated when the line-to-line correlation processing step detects adjacent lines with a high correlation coefficient. This implies that the transducer is likely stationary, and the proximal end of the catheter is turning at a nearly constant velocity. First, one of the two adjacent lines is discarded, in step S910, and an index "i" that starts the deceleration profile is initialized, in step S920. The deceleration is assumed to occur over a given number of lines, for example, 10 lines, as shown in the exemplary acceleration/deceleration profile 900. A small adjustment may be made to the angle of the line that is 10 lines prior to the discarded line to account for the assumed deceleration that occurs prior to the discarded line, in step S930. The index "i" is incremented, in step S940, and a larger angle is subtracted from the next line until the assumed deceleration brings the transducer angular velocity to substantially zero at the location of the discarded line. At this point, a large increment followed by decreasing increments are subtracted from the angles of the respective lines until the index is 10 lines away from the discarded line, in step S950, as the transducer accelerates. Once the full acceleration/deceleration profile 900, in this example, 10 deceleration adjustments and 10 acceleration adjustments have been used to adjust the data table, in step S950, and the data table is returned to the line-to-line correlation processing step, in step S960, to search for the next redundant line.

Proper implementation of the acceleration/deceleration profile 900 may also help ensure precise orientation of a rotating device inserted in a cavity as rotation of the device is interrupted to, for example, more closely examine and/or remove tissue or plaque from a particular portion, such as may be done when, for example, using an ablation device in combination with an imaging system, when precise placement is critical. More particularly, as the imaging device rotates within the cavity and a corresponding image is displayed to an interventionalist for examination, the interventionalist may choose to interrupt rotation of the device for more close examination and/or to remove or sample tissue at a particular location. However, as discussed above, when rotation at the proximal end of the device is stopped, the distal end of the device may experience some delay before its corresponding rotation is stopped, and thus may continue to rotate for a short period after rotation at the proximal end is stopped. Without correction using the appropriate acceleration/deceleration profile 900, this delay at the proximal end may result in imprecise, inaccurate positioning of the imaging and/or ablation device.

The invention as embodied and broadly described herein allows NURD to be significantly reduced, and/or substantially eliminated without significant increases in system complexity and cost. The resulting significant reduction or elimination of NURD provides a more accurate, reliable measure of angular orientation and image of anomalies observed during inspection of the vasculature, thus providing more efficient diagnosis and more appropriate treatment options.

The foregoing embodiments and advantages are merely exemplary and are not to be construed as limiting the invention. The present teaching can be readily applied to other types of apparatuses. The description of the invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. A method for reducing distortion in a device configured to image an interior portion of a cavity, comprising:
   positioning an imaging device within the cavity;
   directing a pulse from the imaging device toward a portion to be imaged;
   collecting data returned from the portion;
   rotating the imaging device in a first direction;
   changing the rotation direction of the imaging device such that the imaging device rotates in a second direction opposite the first direction; and
   reducing non-uniform rotational distortion (NURD) generated by rotation of the device in a resulting image, wherein reducing the NURD includes reducing angular geometric distortion in the resulting image by substantially eliminating all redundant data from the data returned from the portion,
   wherein reducing angular geometric distortion in a resulting image comprises performing at least one of:
      removing a minimum amount of backlash NURD that is generated when the rotational direction of the device is changed based on a predetermined backlash NURD data associated with the device; and
      performing angular correlation to remove backlash NURD that is generated when rotational direction of the device is changed; and
   displaying the resulting image on a display.

2. The method of claim 1, wherein collecting data returned from the portion comprises collecting line data corresponding to each angle of rotation.

3. The method of claim 2, wherein collecting line data corresponding to each angle of rotation further comprises storing the angle and corresponding line data in a data table.

4. The method of claim 3, wherein collecting line data corresponding to each angle of rotation and storing the angle and corresponding line data in a data table comprises:
   initializing a data table with a last line buffer and initializing a counter;
   determining angle data associated with the counter and obtaining line data associated with the angle data;
   writing the angle data and associated line data to the data table;
   incrementing the counter; and
   repeating the determining, writing, and incrementing steps until reaching an end of data input condition.

5. The method of claim 4, wherein reaching an end of data input condition comprises at least one of receiving a predetermined number of lines, receiving a predetermined number of 360 degree image frames, exceeding a predetermined time interval, completing a predetermined number of direction reversals, or receiving no input activity for a predetermined amount of time.

6. The method of claim 3, further comprising scan converting the data table and displaying a corresponding image of the data table, wherein the corresponding image of the data table is the resulting image.

7. The method of claim 3, wherein performing at least one of removing a minimum amount of backlash NURD that is generated when the rotational direction of the device is changed based on a predetermined backlash NURD data associated with the device and performing angular correlation to remove backlash NURD that is generated when the rotational direction of the device is changed comprises:
   removing a minimum amount of backlash NURD that is generated when the rotational direction of the device is changed based on a predetermined backlash NURD data associated with the device.

8. The method of claim 7, wherein removing a minimum amount of backlash NURD that is generated when the rotational direction of the device is changed comprises:
   sensing the change in a rotational direction of the device;
   removing a minimum amount of backlash NURD based on a previously stored table of backlash data;
   adjusting the angle data;
   rewriting the adjusted angle data to the data table; and
   repeating the sensing, removing, adjusting, and rewriting steps until reaching an end of the data table.

9. The method of claim 8, wherein sensing the change in a rotational direction of the device comprises sensing a change in the angle data contained in the data table.

10. The method of claim 9, wherein sensing a change in the angle data contained in the data table comprises determining that angles in the data table go from sequentially increasing to sequentially decreasing, or from sequentially decreasing to sequentially increasing.

11. The method of claim 9, wherein removing a minimum amount of backlash NURD based on a previously stored table of backlash data and adjusting the angle data comprises:
   obtaining a predetermined backlash angle from the previously stored table of backlash data;
   rewriting the data table to remove angles and corresponding data lines contained within the predetermined backlash angle; and
   adjusting angles for all subsequent rows in the data table.

12. The method of claim 11, wherein adjusting the angles for all subsequent rows in the data table comprises:
   adding a current adjustment angle to an original angle and subtracting the predetermined backlash angle when the rotational direction change was from clockwise to counterclockwise; and
   adding the current adjustment angle to the original angle and adding the predetermined backlash angle when the rotational direction change was from counterclockwise to clockwise.

13. The method of claim 8, wherein performing at least one of removing a minimum amount of backlash NURD that is generated when the rotational direction of the device is changed based on a predetermined backlash NURD data associated with the device and performing angular correlation to remove backlash NURD that is generated when the rotational direction of the device is changed further comprises:
   performing angular correlation to remove backlash NURD that is generated when the rotational direction of the device is changed.

14. The method of claim 13, further comprising applying pre-determined values from an acceleration profile to take into account at least one of deceleration of the device when rotation of the device is interrupted, and acceleration of the device when rotation of the device is initiated.

15. The method of claim 13, further comprising performing line-to-line correlation to remove NURD that is generated as a rotational direction of the device remains substantially constant.

16. The method of claim 8, further comprising performing line-to-line correlation to remove NURD that is generated as a rotational direction of the device remains substantially constant.

17. The method of claim 3, further comprising performing line-to-line correlation to remove NURD that is generated as a rotational direction of the device remains substantially constant.

18. The method of claim 17, wherein removing NURD that is generated as a rotational direction of the device remains substantially constant comprises:
   calculating a line-to-line correlation between adjacent data lines in the data table;
   removing redundant data lines from the data table based on the line-to-line correlation;
   adjusting the angle data based on the data lines removed from the data table; and
   repeating the calculating, removing, and adjusting steps until reaching an end of the data table.

19. The method of claim 18, further comprising applying pre-determined values from an acceleration profile to take into account at least one of deceleration of the device when rotation of the device is interrupted, and acceleration of the device when rotation of the device is initiated.

20. The method of claim 18, wherein the data lines comprise echo data lines, and wherein calculating a line-to-line correlation between adjacent echo data lines in the data table is based on the following formula:

$$LineCorr(n) = EchoData(n, i) \not\Leftrightarrow EchoData(n+1, i)$$
$$= \frac{(1)}{(EchoLineSamples - 1)} \times \sum_{i=1}^{EchoLineSamples} EchoData(n, i) * EchoData(n+1, i)$$

wherein n represents a line in the data table associated with a given angle and echo line.

21. The method of claim 20, further comprising discarding all but the first or last line in the data table until the line-to-line correlation drops below a preset threshold.

22. The method of claim 21, wherein the preset threshold is within a range of approximately 0.75 to 1, and wherein a line-to-line correlation of approximately 0.75 to 1 indicates highly correlated lines, and wherein highly correlated lines are discarded and the remaining lines are reoriented based on a predetermined current adjustment angle value.

23. The method of claim 22, wherein the preset threshold is within a range of approximately 0.90 to 1, and wherein a line-to-line correlation of approximately 0.90 to 1 indicates highly correlated lines, and wherein highly correlated lines are discarded and the remaining lines are reoriented based on a predetermined current adjustment angle value.

24. The method of claim 23, wherein the preset threshold is approximately 1, and wherein a line-to-line correlation of approximately 1 indicates highly correlated lines, and wherein highly correlated lines are discarded and the remaining lines are reoriented based on a predetermined current adjustment angle value.

25. The method of claim 3, wherein performing at least one of removing a minimum amount of backlash NURD that is generated when the rotational direction of the device is changed based on a predetermined backlash NURD data associated with the device and performing angular correlation to remove backlash NURD that is generated when the rotational direction of the device is changed comprises:
   performing angular correlation to remove backlash NURD that is generated when the rotational direction of the device is changed.

26. The method of claim 25, wherein removing a remaining amount of backlash NURD that is generated when the rotational direction of the device is changed comprises:
   sensing the change in a rotational direction of the device;
   reading data from a first sector and reading data from a second sector;
   calculating an angular correlation based on the data read from the first and second sectors, and determining a maximum angular rotation value to align the first and second sectors;
   adjusting the second sector based on the maximum angular rotation value;
   rewriting the data table to remove redundant lines and adjust remaining angles; and
   repeating the sensing, reading, calculating, adjusting, and rewriting steps until reaching an end of the data table.

27. The method of claim 26, wherein adjusting the second sector based on the maximum angular correlation value comprises rotating the second sector by the maximum angular correlation value plus a predetermined current adjustment angle.

28. The method of claim 26, wherein the second sector comprises a sector which immediately follows the first sector.

29. The method of claim 28, wherein the first and second sectors are each approximately 40 degrees.

30. The method of claim 26, wherein calculating an angular correlation is based on the equation $$AC_k(\theta) = Sector_k(\theta) \star Sector_{k+1}(\theta\alpha)$$

$$AC_k(\theta) = \sum_{\alpha=-20}^{20} Sector_k(\alpha) \times Sector_{k+1}(\alpha - \theta)$$

wherein k represents the first sector, k+1 represents the second sector, θ represents an angular rotation that aligns the first and second sectors, and α represents the angular index over which the sectors are numerically integrated.

31. The method of claim 26, further comprising performing line-to-line correlation to remove NURD that is generated as a rotational direction of the device remains substantially constant.

32. The method of claim 31, further comprising applying pre-determined values from an acceleration profile to take into account at least one of deceleration of the device when rotation of the device is interrupted, and acceleration of the device when rotation of the device is initiated.

33. An apparatus configured to image an interior portion of a cavity, comprising:
an electronics module configured to generate an electrical pulse to be transmitted;
a transducer assembly configured to transduce the electrical pulse into another form of energy and to direct the transduced pulse toward the interior portion to be imaged, to receive the returned reflections of the transduced pulse from the portion, to transduce the energy received into an electrical signal and to send and receive corresponding electrical data sent to and returned from the portion, wherein the transducer assembly is bi-directional such that it is configured to rotate in a first rotational direction and a second rotational direction opposite the first rotational direction;
a processor configured to receive the corresponding electrical data from the transducer assembly, to digitize the data, and to scan convert the data to form a corresponding image, wherein the processor is configured to reduce angular geometric distortion in the scan converted image due to non-uniform rotational distortion (NURD) caused by rotation of the transducer assembly by substantially eliminating redundant data from the data returned from the portion including at least one of:
removing a minimum amount of backlash NURD that is generated when the rotational direction of the device is changed based on a predetermined mined backlash NURD data associated with the device; and
performing angular correlation to remove backlash NURD that is generated when the rotational direction of the device is changed; and
a display device configured to display the scan converted image.

34. The apparatus of claim 33, wherein the processor comprises:
a data collection processing unit; and
at least one of:
a backlash and windup NURD removal processing unit;
an angular correlation processing unit; and
a line-to-line correlation processing unit.

35. The apparatus of claim 34, wherein the processor comprises:
a backlash and windup NURD removal processing unit.

36. The apparatus of claim 35, wherein the processor further comprises an angular correlation processing unit.

37. The apparatus of claim 36, wherein the processor further comprises a line-to-line correlation processing unit.

38. The apparatus of claim 33, wherein the processor further comprises a line-to-line correlation processing unit.

39. The apparatus of claim 34, wherein the processor comprises:
an angular correlation processing unit.

40. The apparatus of claim 39, wherein the processor further comprise a line-to-line correlation processing unit.

41. The apparatus of claim 34, wherein the processor comprises:
a line-to-line correlation processing unit.

42. The apparatus of claim 35, wherein the backlash and windup NURD removal processing unit is configured to remove the minimum amount of backlash NURD generated when the rotational direction of the transducer assembly is changed.

43. The apparatus of claim 39, wherein the angular correlation processing unit is configured to perform the angular correlation to remove backlash NURD generated when the rotational direction of the transducer assembly is changed.

44. The apparatus of claim 43, wherein the processor is configured to read data taken from a first sector and a second sector of a rotation of the transducer assembly, to calculate an angular correlation coefficient based on the data read from the first and second sectors, and to align the first and second sectors based on a maximum angular correlation value derived from the angular correlation coefficients.

45. The apparatus of claim 44, wherein the processor is further configured to rewrite the data to remove redundant lines and adjust the remaining angles based on the angular correlation coefficient and the maximum angular correlation value.

46. The apparatus of claim 44, wherein the second sector comprises a sector which immediately follows the first sector.

47. The apparatus of claim 42, wherein the processor is configured to obtain a predetermined backlash angle from a previously stored table of backlash data and to remove the angles and corresponding data contained within the predetermined backlash angle from the data returned from the portion so as to remove a minimum amount of backlash NURD.

48. The apparatus of claim 34, wherein the line-to-line correlation processing unit is configured to remove NURD that is generated as the rotational direction of the transducer assembly remains substantially constant.

49. The apparatus of claim 48, wherein the processor is configured to calculate a line-to-line correlation coefficient between adjacent lines of data, and to remove redundant data lines based on the line-to-line correlation coefficient.

50. The method of claim 49, wherein the processor is further configured to apply pre-determined values from an acceleration profile to take into account at least one of deceleration of the device when rotation of the device is interrupted, and acceleration of the device when rotation of the device is initiated.

51. The apparatus of claim 49, wherein the processor is further configured to adjust angle data based on the removed redundant data lines.

52. The apparatus of claim 49, wherein the processor is configured to remove redundant lines when the line-to-line correlation coefficient is within a range of approximately 0.75 to 1.

53. The method of claim 52, wherein the processor is configured to remove redundant lines when the line-to-line correlation coefficient is within a range of approximately 0.90 to 1.

54. The method of claim 53, wherein the processor is configured to remove redundant lines when the line-to-line correlation coefficient is approximately 1.

55. The apparatus of claim 33, wherein the processor is configured to store data in a data table, wherein the data table includes a predetermined number of lines, and wherein the processor is configured to receive and store angle and corresponding line data for each angle in the data table.

56. The apparatus of claim 55, wherein the processor is configured to sense the change in the rotational direction of the transducer assembly based on changes in the angle data contained in the data table.

57. The apparatus of claim 33, wherein at least the transducer assembly is part of an intravascular ultrasound imaging catheter.

58. The apparatus of claim 33, wherein the electronics module and the transducer assembly are sized and shaped for positioning within an inner cavity of a substantially tubular element.

59. The apparatus of claim 33, wherein the transducer assembly is configured to transduce the electrical pulse into an ultrasonic pulse, such that the transduced pulse is the ultrasonic pulse, and direct the ultrasonic pulse toward an interior portion of a cavity to be imaged and to receive the returning ultrasonic pulses and transduce them into electrical pulses and send corresponding echo data returned from the portion to the processor.

60. An apparatus configured to image an interior portion of a cavity, comprising:
    means for directing a pulse toward a portion to be imaged;
    means for collecting data returned from the portion;
    means for rotating the means for directing and the means for collecting in a first rotational direction and a second rotational direction opposite the first direction; and
    means for reducing angular geometric distortion in an image generated from the collected data due to non-uniform rotational distortion (NURD) generated by changes in rotation direction of the apparatus by substantially eliminating redundant data from the data returned from the portion.

61. The apparatus of claim 60, wherein the means for reducing angular geometric distortion in an image generated from the collected data due to non-uniform rotational distortion (NURD) generated by changes in the rotational direction of the means for directing and the means for collecting comprises:
    means for performing at least one of:
        removing a minimum amount of backlash NURD that is generated when the rotational direction of the apparatus is changed based on predetermined backlash NURD data associated with the apparatus; and
        performing angular correlation to remove backlash NURD that is generated when the rotational direction of the apparatus is changed.

* * * * *